US00PP31951P2

(12) United States Plant Patent
Van Dijk

(10) Patent No.: US PP31,951 P2
(45) Date of Patent: Jul. 7, 2020

(54) *ANTHURIUM* PLANT NAMED 'ANTHFESCID'

(50) Latin Name: ***Anthurium andraeanum* L.**
Varietal Denomination: ANTHFESCID

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/501,633

(22) Filed: May 14, 2019

(51) Int. Cl.
*A01H 5/02* (2018.01)
*A01H 6/10* (2018.01)

(52) U.S. Cl.
USPC ..... Plt./365

(58) Field of Classification Search
USPC ..... Plt./365, 369
CPC ... A01H 5/02; A01H 5/00; A01H 5/12; A01H 6/00; A01H 6/10
See application file for complete search history.

(56) References Cited

PUBLICATIONS

Upov Pluto Plant Variety Database Jan. 22, 2020 retrieved on Jan. 22, 2020, retrieved from the Internet at https://www.upov.int/pluto/en/index.jsp, one page (Year: 2020).*
EU Community Plant Variety Rights Application No. 2017/3097, Application n°A201703267, filed Nov. 27, 2017, 8 pages.
EU Community Plant Variety Office Official Gazette, 1.2018, Feb. 15, 2018, cover page and pp. 30, 52.

* cited by examiner

*Primary Examiner* — June Hwu
(74) *Attorney, Agent, or Firm* — Jondle & Associates, P.C.

(57) ABSTRACT

A new *Anthurium* plant named 'ANTHFESCID' particularly distinguished by having large, very shiny, slightly blistered, bright red, orbicular-cordate, and very durable spathes that retain the original color for a very long period of time, dark green, elliptical-cordate, and shiny, durable leaves, white spadices with yellow tips, early and rich flowering continuously throughout the year, and a plant height of 35.0 cm to 40.0 cm is disclosed.

3 Drawing Sheets

Genus and species: *Anthurium andraeanum* L.
Variety denomination: 'ANTHFESCID'.

BACKGROUND OF THE NEW PLANT

The present invention comprises a new and distinct variety of *Anthurium*, botanically known as *Anthurium andraeanum* L., and hereinafter referred to by the variety name 'ANTHFESCID'. The new *Anthurium* plant is a product of a planned breeding program conducted by the inventor in Bleiswijk, the Netherlands. The objective of this breeding program was to create a new plant with a height of 35.0 cm to 40.0 cm having large, very shiny and slightly blistered, bright red, orbicular-cordate, and very durable spathes.

The new variety originated from a cross-pollination made in November 2009 in Bleiswijk, the Netherlands. The female parent was a red *Anthurium* pot plant designated '15817-03' (unpatented), and the male parent was a red *Anthurium* pot plant designated 'ANTHDOTXI' (U.S. Plant Pat. No. PP28,292).

A single plant was selected from the progeny of the stated cross in January 2012. Asexual reproduction of the new variety by tissue culture obtained from callus culture originated on pieces of young leaves in 2014 in Bleiswijk, the Netherlands, has demonstrated that the new variety reproduces true to type with all of the characteristics, as herein described, firmly fixed and retained through successive generations.

Plant Breeder's Rights for this variety have been applied for in the European Union on Nov. 27, 2017, by Applicant who obtained the subject matter disclosed directly from the Inventor. 'ANTHFESCID' has not been made publicly available or sold anywhere in the world more than one year prior to the effective filing date of this application.

SUMMARY OF THE INVENTION

The following are the most outstanding and distinguishing characteristics of this new variety when grown under normal horticultural practices in Bleiswijk, the Netherlands:

1) Large, very shiny and slightly blistered, bright red, orbicular-cordate spathes;
2) White spadices with yellow tips;
3) Green, shiny, elliptical-cordate leaves; and
4) Compact plant structure due to many shoots.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 44-week-old plant grown in a greenhouse in Bleiswijk, the Netherlands, in February 2019. Colors in the photographs may differ from the color values cited in the detailed botanical description, which accurately describe the actual colors of the new variety.

DESCRIPTION OF THE NEW VARIETY

Figure 1:
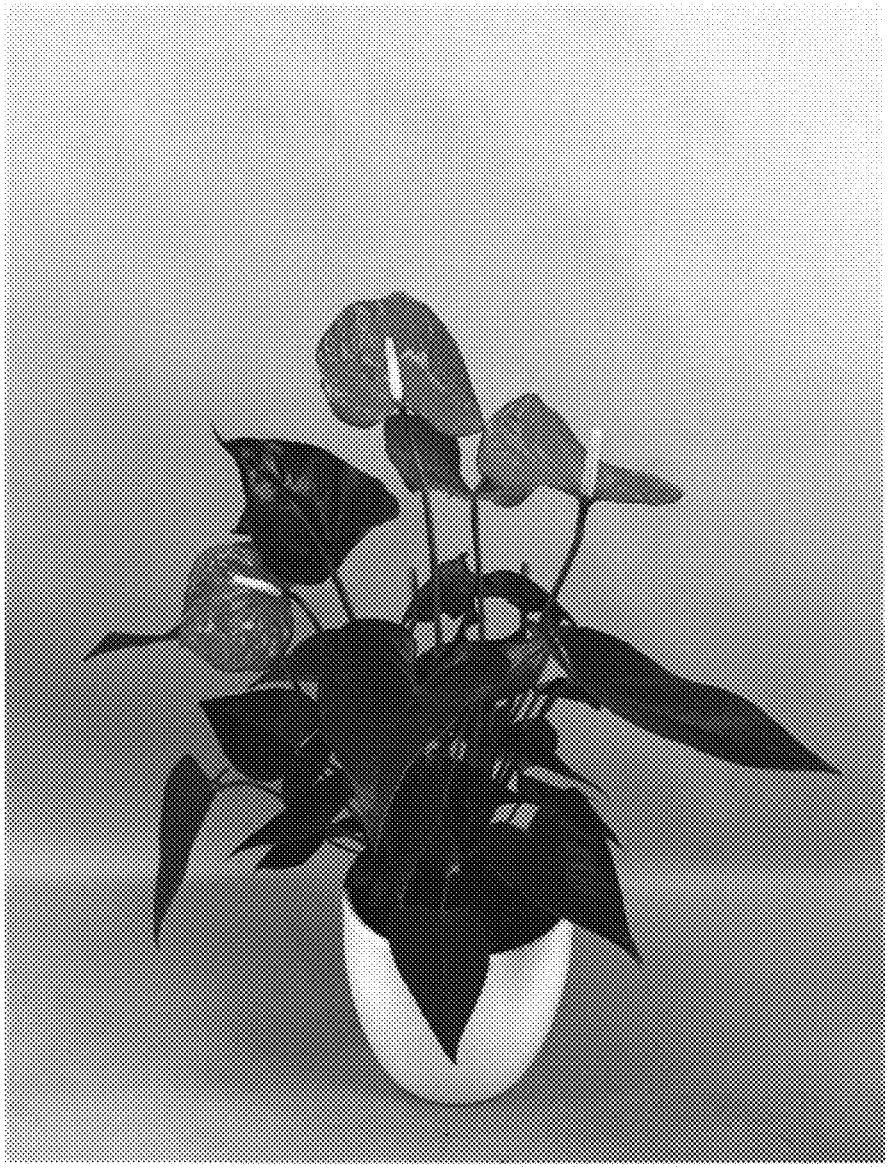
FIG. 1 shows the overall plant habit, including blooms and foliage.
Figure 2:
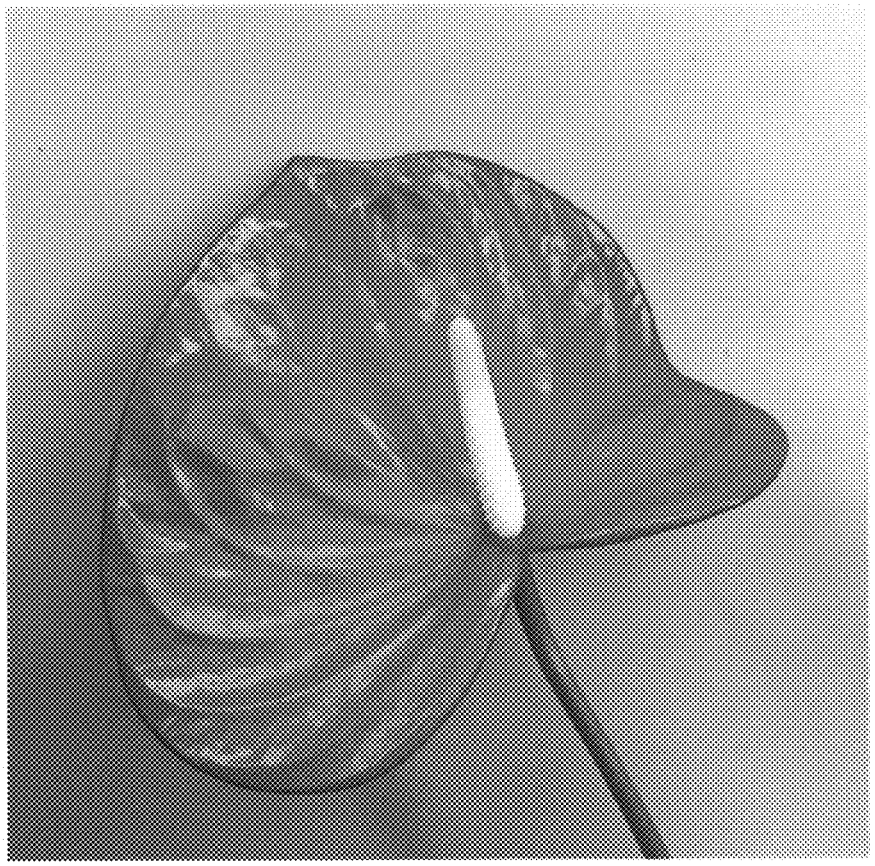
FIG. 2 shows a close-up of the mature spathe.
Figure 3:
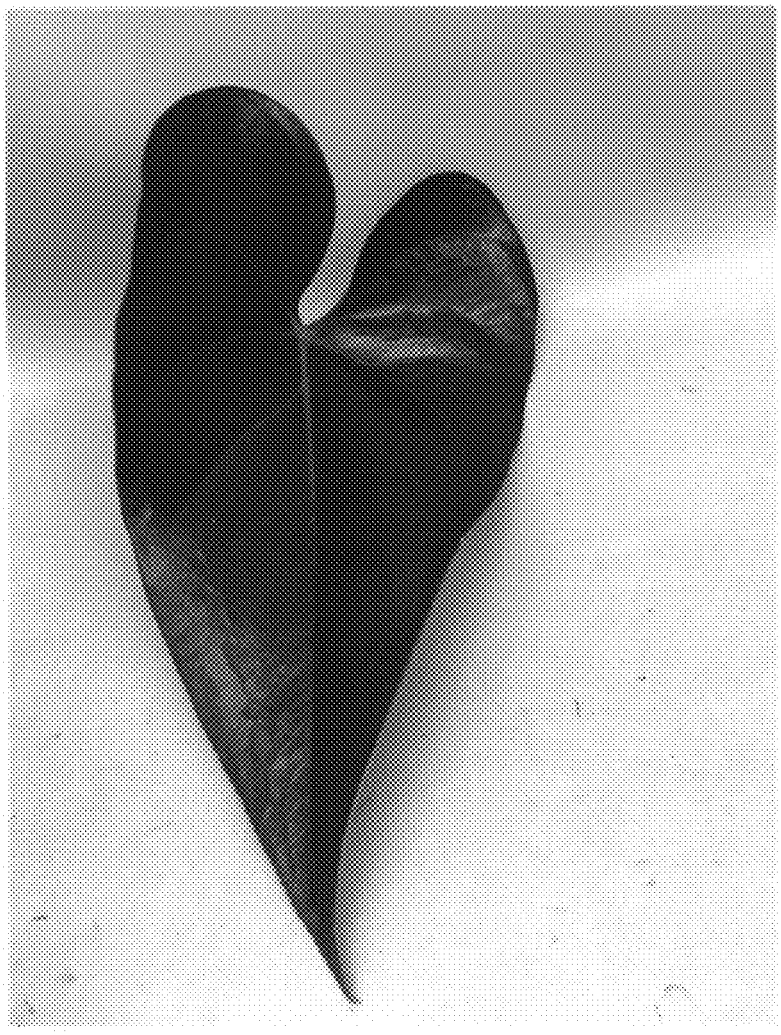
FIG. 3 shows a close-up of the upper leaf blade surface.

The following detailed description sets forth the distinctive characteristics of 'ANTHFESCID'. The data which define these characteristics were collected from asexual reproductions carried out in Bleiswijk, the Netherlands. The plant history was taken on 44-week-old plants which were planted from tissue culture in 14-centimeter (diameter) pots and grown in a glass greenhouse between 19° C. and 24° C. Observations were made in February 2019. Color readings were taken under 5000 lux natural light in the greenhouse. Color references are primarily to The R.H.S. Colour Chart of The Royal Horticultural Society of London (RHS) (2015).

DETAILED BOTANICAL DESCRIPTION

Classification:

*Family.*—Araceae.

*Botanical.*—*Anthurium andraeanum* L.

*Common name.*—*Anthurium.*

*Denomination.*—'ANTHFESCID'.

Parentage:

*Female parent.*—*Anthurium* plant '15817-03' (unpatented).

*Male parent.*—*Anthurium* plant 'ANTHDOTXI' (U.S. Plant Pat. No. 28,292).

Plant:

*Propagation.*—Tissue culture.

*Root description.*—Fleshy, light yellow colored roots with a touch of yellowish-pink and small hairy lateral roots having yellow colored root tips.

*Time to produce a finished flowering plant.*—42 to 46 weeks after planting in a 14-cm (diameter) pot.

*Growth habit.*—Upright.

*Height* (*measured from soil, including inflorescence*).—35.0 cm to 40.0 cm.

*Width* (*measured from leaf tips*).—35.0 cm to 40.0 cm.

Leaves:

*Immature leaves.*—Length: 15.0 cm to 18.0 cm. Width: 8.5 cm to 9.5 cm. Color: Upper surface: RHS 146A. Lower surface: RHS 146B. Texture (both upper and lower surfaces): Shiny.

*Mature leaves.*—Length (fully expanded): 20.0 cm to 23.0 cm. Width: 10.5 cm to 11.5 cm. Shape: Elliptical cordate. Apex: Acuminate. Base: Cordate. Leaf blade angle with the petiole: Between 120 degrees and 140 degrees. Leaf margin: Entire. Color: Upper surface: RHS 147A. Lower surface: RHS 146A. Texture (upper surface): Shiny, leathery, and thick. Blistering (upper surface): Absent. Venation: Pinnate veining; the mid-vein and primary veins (the veins that radiate out from the junction of petiole and leaf) protrude at the underside of the leaf blade. Venation color: Upper surface: RHS 144A. Lower surface: RHS 144B.

*Lobes.*—Present. Arrangement: Leaf blade has two lobes extending past the petiole. The lobes are non-touching. Length of lobes of mature leaf blades: 3.5 cm to 4.5 cm. Width of lobes of mature leaf blades: 5.0 cm to 6.0 cm. Distance from petiole/leaf junction to highest point on lobes of mature leaf: 3.0 cm to 5.0 cm.

*Petiole.*—Cross-section: Round. Diameter: 0.4 cm to 0.5 cm. Length: 17.0 cm to 20.0 cm for a mature leaf size. Color:. Mature leaf: RHS 144A. Immature leaf: RHS 144B. Cataphyll color surrounding the petiole: Outside: RHS 144B with a touch of red (RHS 182B) toward the tip. Inside: RHS 144D.

*Geniculum.*—Length: 2.0 cm to 2.5 cm. Width: 0.5 cm to 0.6 cm. Color: RHS 144B.

Inflorescence:

*Arrangement.*—Single.

*Flowering habit* (*length of flowering season*).—Continuous.

*Number of inflorescences per plant.*—4 to 6.

*Fragrance.*—Absent.

*Longevity of inflorescence on plant.*—Over a year.

Spathe:

*Buds.*—The spathe is tightly rolled around the spadix and extrudes from the peduncle sheath.

*Arrangement.*—Spathe angle with the peduncle is between 100 degrees and 130 degrees; the spathe stands on a wiry peduncle about 1.0 cm to 4.0 cm above the foliage.

*Shape.*—Orbicular cordate.

*Apex.*—Mucronate.

*Base.*—Cordate.

*Texture.*—Very shiny and slightly blistered.

*Margin.*—Undulated.

*Size.*—Length: 11.0 cm to 12.0 cm. Width: 11.0 cm to 12.0 cm.

*Lobes.*—Present. Arrangement: The spathe has two lobes extending past the peduncle. The lobes are non-touching. Length: 1.0 cm to 2.0 cm. Width: 5.0 cm to 6.0 cm.

*Color.*—Just fully open: Upper surface: RHS N45B. Lower surface: RHS N45C. This bright red color remains for a very long period, at least more than 30 weeks after opening.

Peduncle:

*Shape.*—Erect.

*Cross-section.*—Round.

*Length.*—23.0 cm to 28.0 cm.

*Diameter.*—0.4 cm to 0.5 cm.

*Color.*—RHS 144B.

*Anthocyanin.*—Weak.

Flowering time:

*General.*—One small, rooted, untreated tissue culture plant of 8.0 cm tall will flower, depending on the season, after 42 to 46 weeks and 4 to 5 blossoms appear. More blossoms appear after some additional weeks so that a full flowering and commercial plant will have 5 to 6 bright red spathes. Smaller blossoms may occur on immature plants.

Spadix:

*Size.*—Length: 3.5 cm to 4.0 cm (depending on flower size). Width (at apex): 0.5 cm to 0.6 cm. Width (at base): 0.6 cm to 0.7 cm.

*Shape.*—Columnar.

*Angle of spadix tip with peduncle.*—160 degrees to 180 degrees.

*Texture.*—When the spathe is unfurling the spadix is smooth. When the spadix matures, small stigmata protrude. The stigmata are evenly distributed around the spadix. The spadix matures from base to top, slowly giving the spadix a somewhat rough appearance.

*Color.*—Immature: RHS 12A. Mature: RHS NN155A. Ages to: RHS 144C.

Flowers:

*Quantity per spadix.*—120 to 150.

*Spadix flower arrangement.*—Bisexual, rounded in cross-section.

*Shape.*—Rounded.

*Size.*—Length: 0.05 cm to 0.10 cm. Diameter (maximum): 0.10 cm.

*Color.*—RHS 156D.

Reproductive organs:

*Stamens.*—Not visible.

*Pollen amount.*—Absent.

*Pistil.*—Quantity: 120 to 150. Length: Less than 0.01 cm. Color: RHS 156D.

*Style.*—Not observed to date.

*Stigma.*—Shape: Ovoid. Diameter: Less than 0.01 cm. Color: RHS 156D.

*Ovary.*—Rarely visible.

*Ovary color.*—Not measured.

Fruit and seed set: None observed to date.

Disease and pest resistance: No specific resistance or susceptibility observed to pathogens or pests common to *Anthurium* under commercial conditions.

COMPARISON WITH PARENTAL AND SIMILAR COMMERCIAL VARIETIES

'ANTHFESCID' differs from the female parent plant '15817-03' (unpatented) in that 'ANTHFESCID' has a smaller leaf blade angle with the petiole and a smaller peduncle diameter than '15817-03'.

'ANTHFESCID' differs from the male parent plant 'ANTHDOTXI' (U.S. Plant Pat. No. 28,292) in that 'ANTHFESCID' has green cataphylls with a touch of red toward the tip, whereas 'ANTHDOTXI' has red cataphylls. Additionally, 'ANTHFESCID' has a larger peduncle diameter than 'ANTHDOTXI'.

'ANTHFESCID' differs from similar commercial variety 'ANTHDASYM' (U.S. Plant Pat. No. 28,224) in that 'ANTHFESCID' has green cataphylls with a touch of red toward the tip, and orbicular-cordate spathes that are RHS N45B and have mucronate apexes, whereas 'ANTHDASYM' has reddish-orange cataphylls, and cordate spathes that are RHS 46A and have acuminate apexes.

'ANTHFESCID' differs from similar commercial variety 'ANTHCITOK' (unpatented) in that 'ANTHFESCID' has green cataphylls with a touch of red toward the tip, and orbicular-cordate spathes with mucronate apexes, whereas 'ANTHCITOK' has green cataphylls, and cordate spathes with acuminate apexes.

I claim:

1. A new and distinct variety of *Anthurium* plant named 'ANTHFESCID', substantially as illustrated and described herein.

* * * * *